US010578414B2

(12) United States Patent
Takahama (10) Patent No.: US 10,578,414 B2
(45) Date of Patent: Mar. 3, 2020

(54) INNER-WALL MEASURING INSTRUMENT AND OFFSET-AMOUNT CALCULATION METHOD (71) Applicant: MITUTOYO CORPORATION, Kanagawa (JP)

(72) Inventor: Yasuhiro Takahama, Kanagawa (JP)

(73) Assignee: MITUTOYO CORPORATION, Kanagawa (JP)

(*) Notice: Subject to any disclaimer, the term of this patent is extended or adjusted under 35 U.S.C. 154(b) by 383 days.

(21) Appl. No.: 15/439,120

(22) Filed: Feb. 22, 2017

(65) Prior Publication Data
US 2017/0248399 A1 Aug. 31, 2017

(30) Foreign Application Priority Data
Feb. 25, 2016 (JP) .................. 2016-034776

(51) Int. Cl.
G01B 3/22 (2006.01)
G01B 5/06 (2006.01)
(Continued)

(52) U.S. Cl.
CPC .............. G01B 3/22 (2013.01); G01B 5/003 (2013.01); G01B 5/061 (2013.01); G01B 5/12 (2013.01);
(Continued)

(58) Field of Classification Search
CPC ...... G01B 3/22; G01B 11/2441; G01B 11/12; G01B 11/0608; G01B 5/061; G01B 5/003;
(Continued)

(56) References Cited

U.S. PATENT DOCUMENTS 4,908,951 A * 3/1990 Gurny ................. G01B 11/005
33/1 M
5,125,035 A * 6/1992 McCarthy ........ G01N 21/95692
348/94
(Continued)

FOREIGN PATENT DOCUMENTS

JP 2007-530960 11/2007
JP 2009-216548 9/2009
(Continued)

OTHER PUBLICATIONS

Japanese Office Action dated Nov. 5, 2019 issued in Japanese Patent Application No. 2016-034776, and corresponding English translation.

Primary Examiner — Nimeshkumar D Patel
Assistant Examiner — Tania Courson
(74) Attorney, Agent, or Firm — Greenblum & Bernstein, P.L.C.

(57) ABSTRACT

An inner-wall measuring instrument includes: a placement surface on which an object to be measured is placed; a base relatively movable with respect to the placement surface in three axis directions orthogonal to one another; a touch probe that is disposed at a first position of the base and brought into contact with the object; an image probe that is disposed at a second position of the base and capable of imaging the object with a direction parallel to the placement surface being an imaging direction; a rotational drive unit that rotates the image probe around an axis extending in a direction perpendicular to the placement surface; a linear drive unit that moves the image probe in the imaging direction; and a calculator that calculates an offset amount between the touch probe disposed at the first position and the image probe disposed at the second position.

18 Claims, 10 Drawing Sheets (51) Int. Cl.
*G01B 5/12* (2006.01)
*G01B 5/00* (2006.01)
*G01B 11/06* (2006.01)
*G01B 11/24* (2006.01)
*G01B 11/12* (2006.01)
*G01N 21/954* (2006.01)
*G01B 11/14* (2006.01)
*G01M 15/04* (2006.01)

(52) U.S. Cl.
CPC .......... *G01B 11/0608* (2013.01); *G01B 11/12* (2013.01); *G01B 11/14* (2013.01); *G01B 11/2441* (2013.01); *G01N 21/954* (2013.01); *G01M 15/042* (2013.01)

(58) Field of Classification Search
CPC ........ G01B 5/12; G01B 11/14; G01N 21/954; G01M 15/042
See application file for complete search history.

(56) References Cited

U.S. PATENT DOCUMENTS

| | | | | |
|---|---|---|---|---|
| 5,305,091 A * | 4/1994 | Gelbart | ................ | G01B 11/002 250/559.33 |
| 5,615,489 A * | 4/1997 | Breyer | ................... | G01B 5/012 33/503 |
| 5,805,287 A * | 9/1998 | Pettersen | ............. | G01B 11/245 356/614 |
| 5,825,017 A * | 10/1998 | Pryor | ....................... | F02F 1/24 250/208.1 |
| 5,825,666 A * | 10/1998 | Freifeld | ............... | G01B 11/005 702/153 |
| 6,067,165 A * | 5/2000 | Matsumiya | .......... | G01B 11/005 356/399 |
| 6,961,670 B2 * | 11/2005 | Sasaki | ...................... | G01B 5/20 324/754.03 |
| 7,012,700 B2 * | 3/2006 | De Groot | ........... | G01B 11/2441 356/512 |
| 7,428,057 B2 * | 9/2008 | De Lega | ................ | G01B 9/023 356/497 |
| 7,895,764 B2 * | 3/2011 | Ishizu | .................... | G01B 5/008 33/557 |
| 8,139,229 B2 * | 3/2012 | Yamagata | .............. | G01B 11/03 356/601 |
| 8,358,424 B2 * | 1/2013 | Toyoda | ................ | G01B 11/026 356/614 |
| 8,650,939 B2 * | 2/2014 | Matsumiya | ........... | G01B 5/008 73/104 |
| 9,341,460 B2 * | 5/2016 | Kurihara | ............... | G01B 5/016 |
| 9,778,023 B2 * | 10/2017 | Osaki | .................... | G01B 11/24 |
| 9,863,763 B2 * | 1/2018 | Nishikawa | ......... | G05B 19/4097 |
| 10,001,356 B2 * | 6/2018 | Tanaka | ................ | G01B 21/047 |
| 10,274,313 B2 * | 4/2019 | Sakai | ................... | G01B 11/14 |
| 2005/0151963 A1 * | 7/2005 | Pulla | ...................... | G01B 21/04 356/139.03 |
| 2006/0196062 A1 * | 9/2006 | Nishibashi | ........... | B23Q 1/5462 33/502 |
| 2007/0086620 A1 * | 4/2007 | Arai | ....................... | G01B 5/008 382/100 |
| 2008/0228441 A1 | 9/2008 | Lugtenburg | | |
| 2011/0085178 A1 | 4/2011 | Takahashi | | |
| 2015/0276393 A1 * | 10/2015 | Nishikawa | ......... | G05B 19/4097 29/888.06 |
| 2017/0248419 A1 * | 8/2017 | Kudo | ...................... | G01B 21/20 |
| 2019/0113333 A1 * | 4/2019 | Takahama | ......... | G01B 9/02068 |

FOREIGN PATENT DOCUMENTS

JP 2011-085403 4/2011
JP 5350169 8/2013

* cited by examiner

INNER-WALL MEASURING INSTRUMENT AND OFFSET-AMOUNT CALCULATION METHOD

CROSS REFERENCE TO RELATED APPLICATIONS

This application claims the benefit of Japanese Priority Patent Application JP 2016-034776 filed Feb. 25, 2016, the entire contents of which are incorporated herein by reference.

BACKGROUND

The present technology relates to an inner-wall measuring instrument capable of, for example, measuring an inner wall of an engine cylinder or the like and to an offset-amount calculation method applicable thereto.

From the past, measuring instruments including a plurality of types of probes have been used. For example, Japanese Patent Application Laid-open No. 2009-216548 (hereinafter, referred to as Patent Document 1) has described a surface profile measuring instrument including a probe holder to which a laser displacement probe, a touch probe, and an image probe are attached. In this surface profile measuring instrument, the probe holder is provided with a probe selection mechanism. The probe selection mechanism is capable of selectively moving a probe to be used for measurement to a predetermined probe selection position and retracting the other probes from the probe selection position. With this, it becomes possible to maintain measurable ranges in common with the probes without increasing the size of the instrument (paragraphs [0015], [0016], and [0021] in specification, and FIGS. 3 and 4, etc. of Patent Document 1).

Moreover, Japanese Patent No. 5350169 (hereinafter, referred to as Patent Document 2) has described an offset-amount calculation method, in which, regarding a surface profile measuring instrument including a contact-type detector including a stylus and an image probe, an offset amount between the contact-type detector and the image probe can be correctly determined (paragraphs [0028] to [0032] and [0021] in specification, FIGS. 8 to 10, etc. of Patent Document 2).

SUMMARY

A technology that enables the measuring instrument including the plurality of probes as described above to, for example, highly accurately measure a surface profile, a bore radius, or the like of an inner wall of an engine cylinder or the like is desirable.

In view of the above-mentioned circumstances, there is a need for providing an inner-wall measuring instrument capable of measuring an inner wall with high accuracy and an offset-amount calculation method applicable thereto.

According to an embodiment of the present technology, there is provided an inner-wall measuring instrument including a placement surface, a base, a touch probe, an image probe, a rotational drive unit, a linear drive unit, and a calculator.

On the placement surface, an object to be measured is placed.

The base is relatively movable with respect to the placement surface in three axis directions orthogonal to one another.

The touch probe is disposed at a first position of the base and brought into contact with the object to be measured.

The image probe is disposed at a second position of the base and capable of imaging the object to be measured with a direction parallel to the placement surface being an imaging direction.

The rotational drive unit rotates the image probe around an axis extending in a direction perpendicular to the placement surface.

The linear drive unit moves the image probe in the imaging direction.

The calculator calculates an offset amount between the touch probe disposed at the first position and the image probe disposed at the second position.

In this inner-wall measuring instrument, the touch probe and the image probe capable of performing imaging in the direction parallel to the placement surface are disposed on the base. The image probe is rotated by the rotational drive unit around the axis extending in the direction perpendicular to the placement surface. Moreover, the image probe is moved by the linear drive unit in the imaging direction. With this, the object to be measured can be imaged in different imaging directions in the direction parallel to the placement surface. Also, scanning in the imaging directions becomes possible. Moreover, the offset amount between the touch probe and the image probe is calculated by the calculator, and hence an inner wall can be highly accurately measured.

The base may be relatively movable with respect to the placement surface in a first direction perpendicular to the placement surface, a second direction orthogonal to the first direction, and a third direction orthogonal to each of the first direction and the second direction. In this case, the rotational drive unit may rotate the image probe around an axis extending in the first direction.

The movement direction of the base is the same as a direction of a rotation axis of the image probe, and hence highly accurate inner-wall measurement is possible.

The touch probe may include a tip end portion that is brought into contact with the object to be measured. In this case, the image probe may include an imaging optical system that images the object to be measured. Moreover, the calculator may calculate an offset amount between a position of the tip end portion of the touch probe and a focal position of the imaging optical system of the image probe.

With this, it is possible to highly accurately select the touch probe or the image probe, for example.

The imaging optical system may be a light interferometric optical system.

The use of light interference enables a surface profile or the like of the inner wall to be highly accurately measured.

The calculator may calculate each of a first offset amount between a rotation axis of the image probe rotated by the rotational drive unit and a movement axis of the image probe moved by the linear drive unit and a second offset amount between the touch probe and the rotation axis, and calculate the offset amount on the basis of the calculated first and second offset amounts, the first offset amount and the second offset amount being in the direction parallel to the placement surface.

With this, it is possible to accurately calculate the offset amount.

The calculator may calculate the first offset amount on the basis of a result of measurement performed on a first calibration jig by an image probe for calibration in a state in which the image probe for calibration is disposed at the first position, the image probe for calibration being capable of imaging the object to be measured with the direction perpendicular to the placement surface being an imaging direction.

The use of the image probe for calibration enables the first offset amount to be highly accurately calculated.

The calculator may calculate the second offset amount on the basis of a result of measurement performed on a second calibration jig by each of the touch probe and the image probe for calibration in a state in which the image probe for calibration is disposed at the first position.

The use of the image probe for calibration enables the second offset amount to be highly accurately calculated.

The calculator may calculate an offset amount between the touch probe and the image probe in the direction perpendicular to the placement surface on the basis of a result of measurement performed on a third calibration jig by each of the touch probe and the image probe in a state in which the image probe is disposed at the first position.

With this, it is possible to accurately calculate the offset amount.

The calculator may calculate a distance up to a focal position of the image probe on the basis of a result of measurement performed on a fourth calibration jig by the image probe in a state in which the image probe is disposed at the first position, and calculate the offset amount on the basis of the calculated distance up to the focal position.

With this, it is possible to accurately calculate the offset amount.

According to an embodiment of the present technology, there is provided an offset-amount calculation method for calculating an offset amount between a touch probe disposed at a first position of a base, which is relatively movable in three axis directions orthogonal to one another with respect to a placement surface on which an object to be measured is placed, and an image probe disposed at a second position of the base.

The method includes calculating a first offset amount in a direction parallel to the placement surface between a rotation axis and a movement axis of the image probe capable of imaging the object to be measured with the direction parallel to the placement surface being an imaging direction, the image probe being rotated by a rotational drive unit around the rotation axis extending in a direction perpendicular to the placement surface and moved by a linear drive unit along the movement axis extending in the imaging direction.

A second offset amount in the direction parallel to the placement surface between the touch probe and the rotation axis is calculated.

An offset amount between the touch probe and the image probe is calculated on the basis of the calculated first and second offset amounts.

In this offset-amount calculation method, the offset amount between the touch probe and the image probe can be highly accurately calculated on the basis of the first offset amount and the second offset amount.

The step of calculating the first offset amount may include a step of disposing an image probe for calibration at the first position, the image probe for calibration being capable of imaging the object to be measured with the direction perpendicular to the placement surface being an imaging direction, and a step of causing the image probe for calibration to measure a first calibration jig in a state in which the image probe for calibration is disposed at the first position and calculating the first offset amount on the basis of the measurement result.

The use of the image probe for calibration enables the first offset amount to be highly accurately calculated.

The step of calculating the second offset amount may include a step of causing each of the touch probe and the image probe for calibration to measure a second calibration jig in a state in which the image probe for calibration is disposed at the first position and calculating the second offset amount on the basis of the measurement result.

The use of the image probe for calibration enables the second offset amount to be highly accurately calculated.

The offset-amount calculation method may further include calculating an offset amount between the touch probe and the image probe in the direction perpendicular to the placement surface.

With this, it is possible to highly accurately calculate the offset amount between the touch probe and the image probe in each of the three axis directions orthogonal to one another.

The step of calculating the offset-amount in the direction perpendicular to the placement surface may include a step of disposing the image probe at the first position, and a step of causing each of the touch probe and the image probe to measure a third calibration jig in a state in which the image probe is disposed at the first position and calculating the offset amount in the direction perpendicular to the placement surface on the basis of the measurement result.

With this, it is possible to highly accurately calculate the offset amount in the direction perpendicular to the placement surface.

The offset-amount calculation method may further include calculating a distance up to a focal position of the image probe on the basis of a result of measurement performed on a fourth calibration jig by the image probe in a state in which the image probe is disposed at the first position.

With this, it is possible to highly accurately calculate the offset amount between the touch probe and the image probe.

As described above, in accordance with the embodiments of the present technology, it is possible to highly accurately measure an inner wall. It should be noted that the effects described here are not necessarily limitative and may be any effects described in the present disclosure.

DETAILED DESCRIPTION OF EMBODIMENTS

Hereinafter, an embodiment of the present technology will be described with reference to the drawings.

[Configuration of Inner-Wall Measurement Apparatus]

Figure 1:
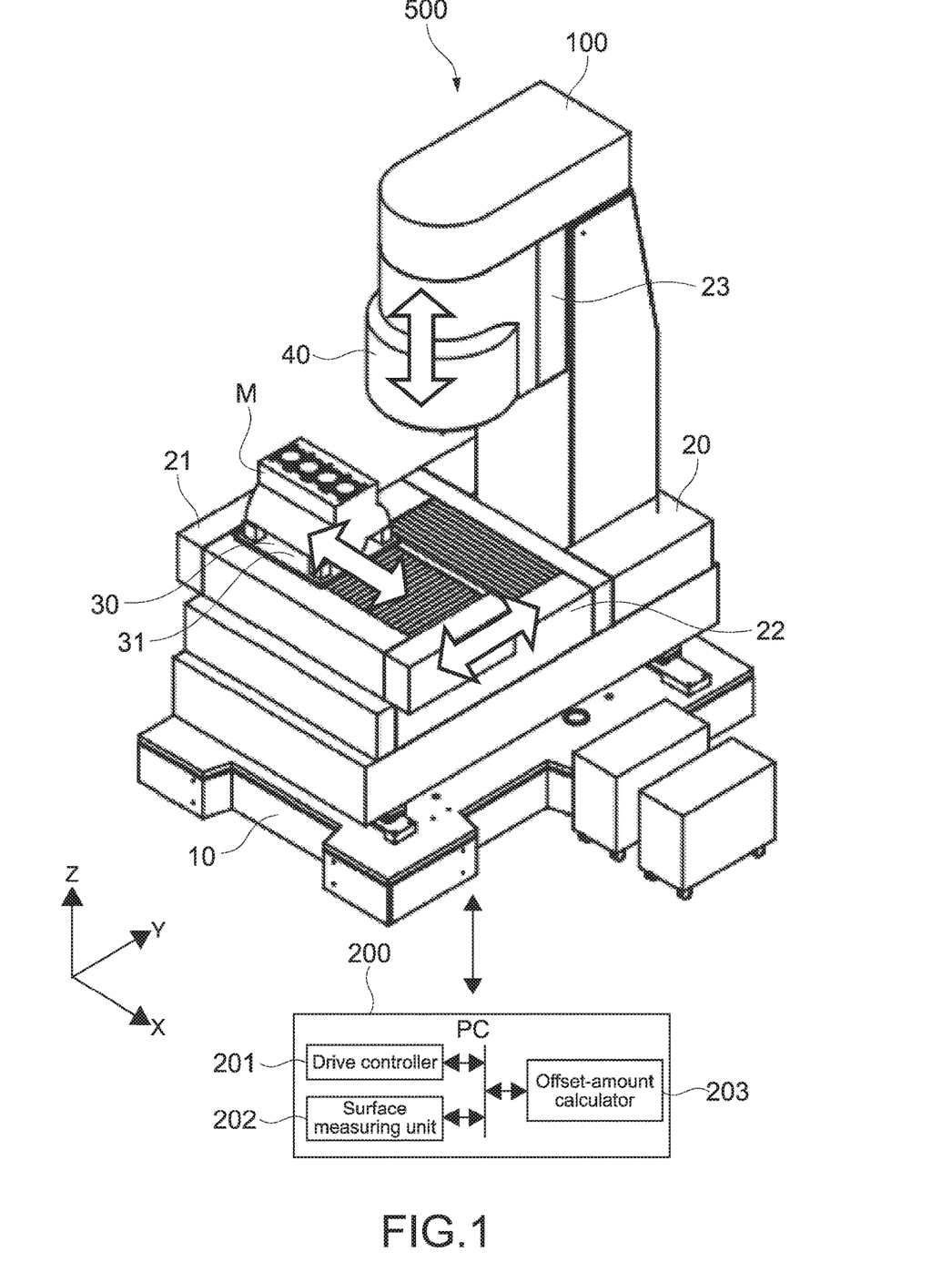
FIG. 1 is a diagram schematically showing an outer appearance of an inner-wall measuring instrument according to an embodiment of the present technology.

FIG. 1 is a diagram schematically showing an outer appearance of an inner-wall measuring instrument according to the embodiment of the present technology. An inner-wall measuring instrument 500 includes a three-dimensional coordinate measuring device 100 and a personal computer (PC) 200. The three-dimensional coordinate measuring device 100 and the PC 200 may be integrally configured. Alternatively, a computer other than the PC 200 may be used.

Figure 2:
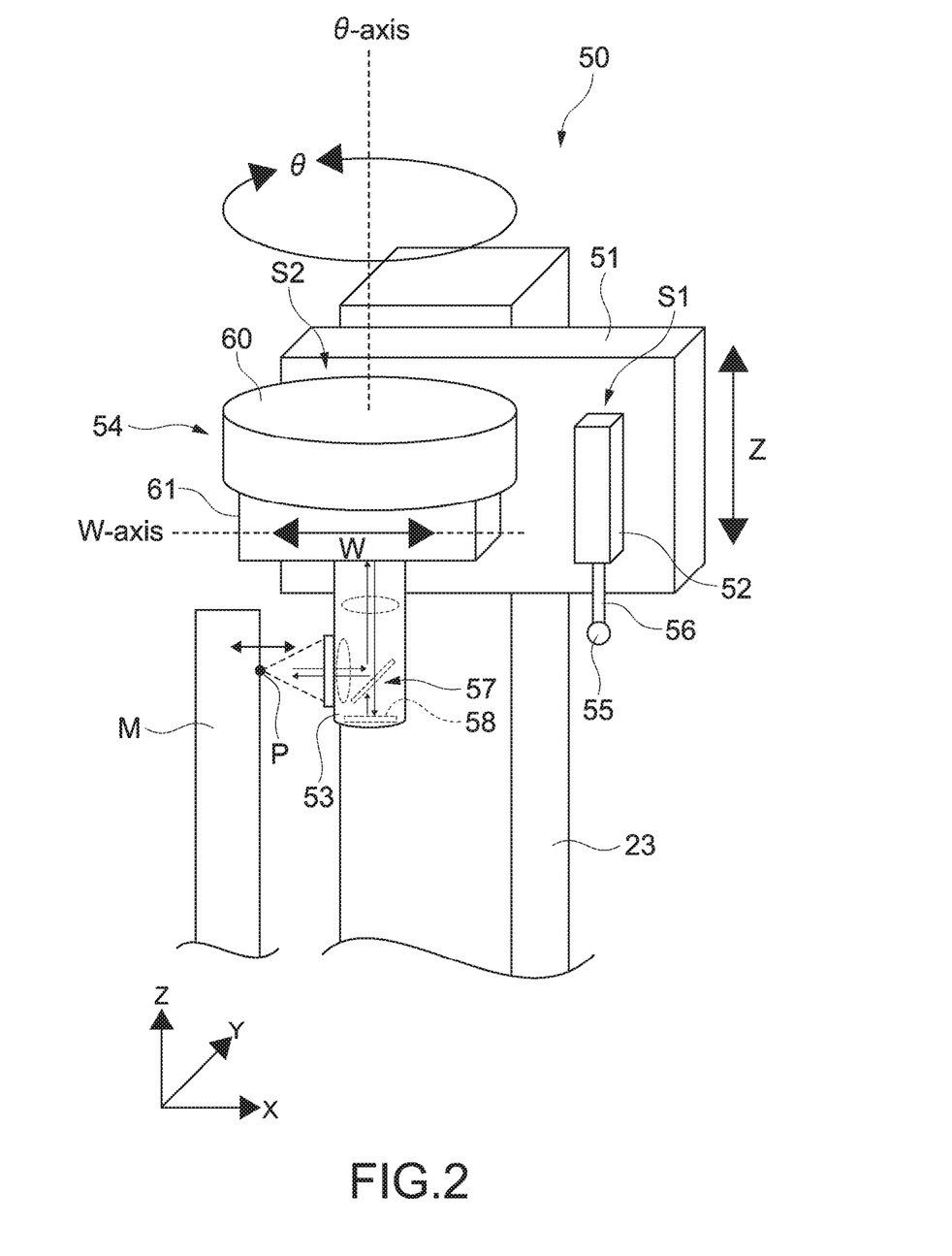
FIG. 2 is a schematic diagram showing an exemplary configuration of a probe head.

The three-dimensional coordinate measuring device 100 includes a base section 10, a three-axis movement mechanism 20, a stage 30, a head cover 40, and a probe head 50 (see FIG. 2). The three-axis movement mechanism 20 is supported by the base section 10.

The three-axis movement mechanism 20 includes an X-axis movement mechanism 21, a Y-axis movement mechanism 22, and a Z-axis movement mechanism 23. The X-axis movement mechanism 21 supports the stage 30 to be movable in an X-direction. The Y-axis movement mechanism 22 supports the X-axis movement mechanism 21 to be movable in a Y-direction. The Z-axis movement mechanism 23 moves the head cover 40 and the probe head 50 in a Z-direction.

The three-axis movement mechanism 20 is controlled by the PC 200, and hence the probe head 50 can perform scanning in a measurement coordinate section formed of three axes of XYZ. That is, it is possible to relatively move the probe head 50 with respect to an object to be measured M placed on the stage 30 in three axis directions of XYZ orthogonal to one another.

Specific configurations of the X-axis movement mechanism 21, the Y-axis movement mechanism 22, and the Z-axis movement mechanism 23 are not limited. Moreover, any configuration may be employed for a configuration of the three-axis movement mechanism 20 as long as the three-axis movement mechanism 20 can cause the probe head 50 to perform scanning in each of the X-, Y-, and Z-directions. Note that, in this embodiment, the Z-direction corresponds to a first direction and the X- and Y-directions respectively correspond to second and third directions.

The three-dimensional coordinate measuring device 100 is provided with position detection mechanisms (not shown) such as linear encoders for the X-, Y-, and Z-directions. The position detection mechanisms output data to the PC 200. This data relates to relative displacement and position of the probe head 50 with respect to the object to be measured M. Specific configurations of the position detection mechanisms are not limited.

The stage 30 includes a placement surface 31 parallel to a horizontal direction (XY-plane direction). The object to be measured M is placed on the placement surface 31. In this embodiment, a cylinder block, which is incorporated in an automobile or the like, is placed on the placement surface 31 as the object to be measured M. The inner wall of the cylinder provided in the cylinder block can be measured by controlling the probe head 50 covered with the head cover 40. The probe head 50 will be described later in detail.

The PC 200 is connected to the three-dimensional coordinate measuring device 100 in an arbitrary connection form. The PC 200 includes hardware necessary for a computer configuration, for example, a central processing unit (CPU), a read only memory (ROM), a random access memory (RAM), and a hard disk drive (HDD) (that are not shown in drawings).

Processing of the PC 200 can be performed, for example, when the CPU loads a predetermined program stored in the ROM, HDD, or the like into the RAM and executes it. As shown in FIG. 1, in this embodiment, a drive controller 201, a surface measuring unit 202, and an offset-amount calculator 203 are configured by the CPU executing a predetermined program. Dedicated hardware may be used for configuring those blocks.

The drive controller 201 controls driving of the mechanisms inside the three-dimensional coordinate measuring device 100. The surface measuring unit 202 measures, on the basis of measurement data or the like output from the three-dimensional coordinate measuring device 100, a surface profile or the like of the object to be measured M. The offset-amount calculator 203 calculates an offset amount between a touch probe 52 and an image probe 53 that are provided in the probe head 50. The offset-amount calculation method will be described later in detail.

Programs are installed in the PC 200 via various recording media, for example. Alternatively, programs may be installed in the PC 200 via the Internet or the like.

FIG. 2 is a schematic diagram showing an exemplary configuration of the probe head 50. The probe head 50 includes a base 51, the touch probe 52, the image probe 53, and a probe supporting mechanism 54. The base 51 is connected to the Z-axis movement mechanism 23 and moved in the Z-direction. When the base 51 is moved, the touch probe 52, the image probe 53, and the probe supporting mechanism 54 are also moved together.

The touch probe 52 is disposed at a first position S1 of the base 51. The touch probe 52 includes a stylus 56 provided with a tip ball 55. The touch probe 52 is attached at the first position S1 such that the stylus 56 extends in the Z-direction.

The touch probe 52 performs scanning in such a manner that the tip ball 55 is held in contact with the object to be measured M. On the basis of XYZ-coordinate information obtained when the contact of the object to be measured M with the tip ball 55 is detected, the shape, the height, or the like of the object to be measured M is calculated. A specific configuration of the touch probe 52 is not limited and any touch probe may be used.

The image probe 53 is disposed at a second position S2 of the base 51 via the probe supporting mechanism 54. In the example shown in FIG. 2, the first position S1 and the second position S2 are set at positions aligned with each other in the X-direction, though not limited thereto.

In this embodiment, a white light interferometer is used as the image probe 53. Thus, as shown in FIG. 2, a white light interferometric optical system 57 is configured inside the image probe 53. The white light interferometric optical system 57 is configured to be capable of imaging the object to be measured M with a direction (XY-plane direction) parallel to the placement surface 31 on which the object to be measured M is placed being an imaging direction. Specifically, a surface of the object to be measured M, which is parallel to the Z-direction and perpendicular to the X-direction, can be measured by the image probe 53.

Moreover, typically, a setting is made such that an optical distance between a focal position P of the white light interferometric optical system 57 and an image sensor (not shown) inside the image probe 53 is equal to an optical distance between a reference surface 58 and the image sensor. As a matter of course, embodiments of the present technology are not limited to such a setting. A specific configuration of the white light interferometric optical system 57, optical members to be used, and the like are not limited and may be appropriately designed.

The probe supporting mechanism 54 includes a rotational drive unit 60 and a linear drive unit 61. The rotational drive unit 60 is capable of rotating the image probe 53 with a $\theta$-axis extending in the Z-direction that is a direction perpendicular to the placement surface 31 being a rotation axis. The rotational drive unit 60 is rotatably disposed at the second position S2 of the base 51 via, for example, a connection member (not shown). A specific configuration of the rotational drive unit 60 is not limited. For example, the rotational drive unit 60 is constituted of a driving source such as a motor, a rotational member that transmits rotational torque, and the like.

The linear drive unit 61 is attached to the rotational drive unit 60. The linear drive unit 61 is capable of moving the image probe 53 along a W-axis extending in one direction. The image probe 53 is attached to the linear drive unit 61 such that a direction of an imaging optical axis is the same as a direction of the W-axis. Thus, the linear drive unit 61 is capable of moving the image probe 53 in the imaging direction. Note that the linear drive unit 61 may be fixed to the rotational drive unit 60 or may be movable in a W-axis direction. A specific configuration of the linear drive unit 61 is not limited and may be arbitrarily designed.

As described above, in this embodiment, the image probe 53 is disposed at the second position S2 of the base 51 via the rotational drive unit 60 and the linear drive unit 61. The rotational drive unit 60 rotates the image probe 53 disposed at the second position S2. The linear drive unit 61 moves the image probe 53 disposed at the second position S2 in one direction.

Figure 3A:
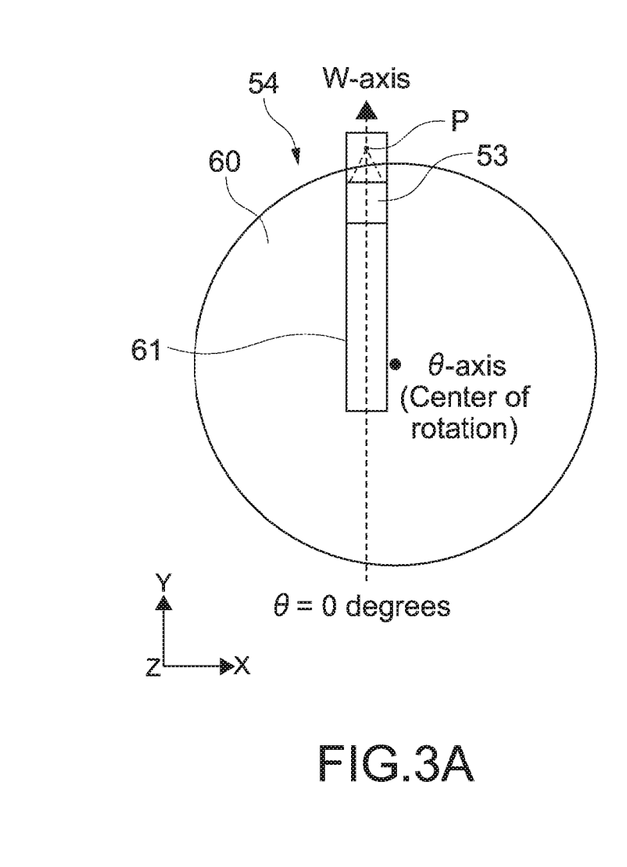
FIGS. 3A and 3B are schematic diagrams each showing a probe supporting mechanism as viewed from above in a Z-direction.
Figure 3B:
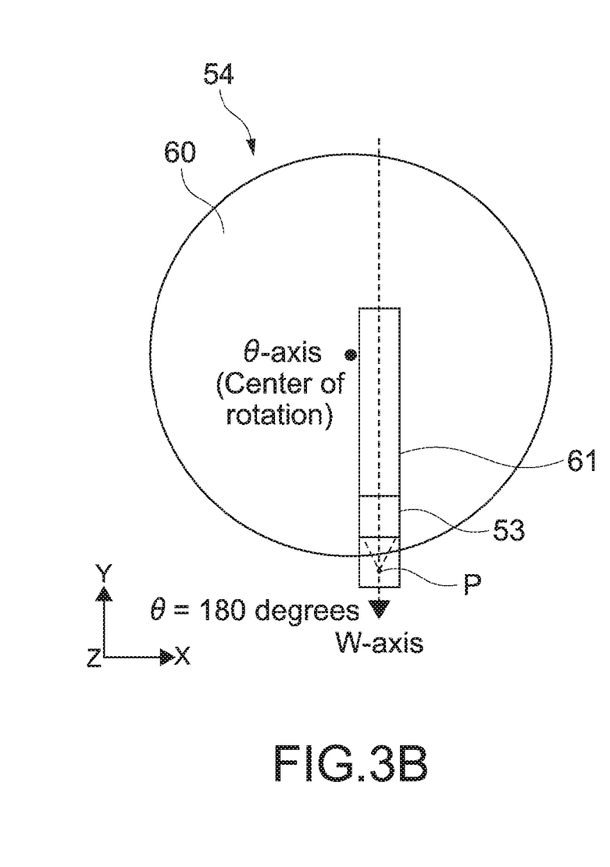

FIGS. 3A and 3B are schematic diagrams each showing the probe supporting mechanism 54 as viewed from above in the Z-direction. In FIGS. 3A and 3B, for the sake of easy understanding, the linear drive unit 61 and the image probe 53 that are positioned below the rotational drive unit 60 are visibly shown. Moreover, the image probe 53 in a rectangular shape is schematically shown.

As shown in FIGS. 3A and 3B, when the rotational drive unit 60 is driven, the linear drive unit 61 and the image probe 53 are rotated about the $\theta$-axis. Thus, the W-axis, which is a moving axis of the image probe 53 moved by the linear drive unit 61, is also rotated.

An angle scale is set around the $\theta$-axis on the basis of a predetermined position. A rotational angle $\theta$ of the image probe 53 in the imaging direction (W-axis direction) can be controlled by the PC 200 controlling the rotational drive unit 60. Moreover, the rotational angle $\theta$ is detected by an angle detection mechanism such as a rotary encoder (not shown) and output to the PC 200.

In this embodiment, when the rotational angle $\theta$ is 0 degrees and 180 degrees, the W-axis extends in the Y-direction and directions of coordinate axes are opposite to each other. When the rotational angle $\theta$ is 90 degrees and 270 degrees, the W-axis extends in the X-direction and the directions of the coordinate axes are opposite to each other. As a matter of course, embodiments of the present technology are not limited to such angle settings.

A predetermined scale is also set on the W-axis. The image probe 53 can be moved to a predetermined position on the W-axis (position of predetermined W-coordinate) by the PC 200 controlling the linear drive unit 61. Moreover, a position (W-coordinate) of the image probe 53 is detected by a position detection mechanism such as a linear encoder (not shown) and output to the PC 200.

Note that the rotational drive unit 60 and the linear drive unit 61 can also be assembled such that the W-axis is on the $\theta$-axis. However, it is actually difficult to precisely position the W-axis on the $\theta$-axis due to assembling error and the like. As will be described later, the offset-amount calculation method according to this embodiment enables an offset amount including the distance between the $\theta$-axis and the W-axis to be calculated.

[Offset-Amount Calculation Method]

The offset-amount calculation method according to this embodiment will be described. In this embodiment, an offset amount between a position of the tip ball 55 and the focal position P is calculated as an offset amount between the touch probe 52 disposed at the first position S1 and the image probe 53 disposed at the second position S2. This offset amount is an amount varied in a manner that depends on the rotational angle $\theta$ of the rotational drive unit 60 and the W-coordinate of the image probe 53. The use of this calculation method enables an offset amount depending on the rotational angle $\theta$ and the W-coordinate to be calculated.

For example, there can also be a case where such an offset amount is calculated and stored in advance as a design value of the three-dimensional coordinate measuring device 100. However, in many cases, the offset amount is actually different from the design value due to dimensional tolerance, assembling error, and the like. The use of the calculation method enables the offset amount to be highly accurately corrected at a predetermined timing, for example, before measurement.

Figure 4:
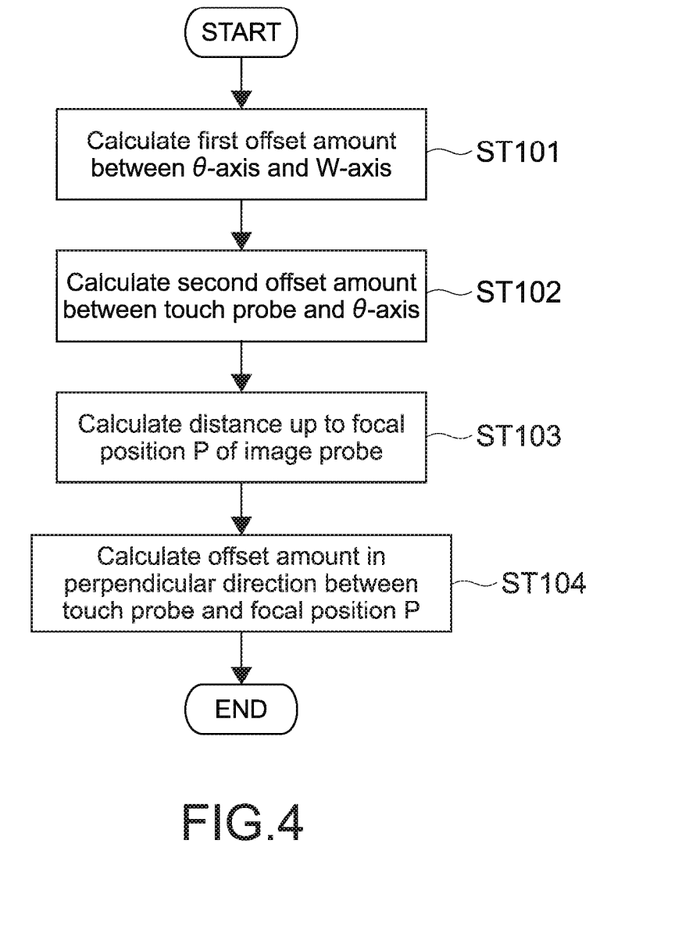
FIG. 4 is a flowchart showing an exemplary offset-amount calculation.

FIG. 4 is a flowchart showing an exemplary offset-amount calculation. First of all, a first offset amount between the $\theta$-axis and the W-axis is calculated (Step 101). The first offset amount is a distance between the $\theta$-axis and the W-axis in the XY-plane direction.

Figure 5A:
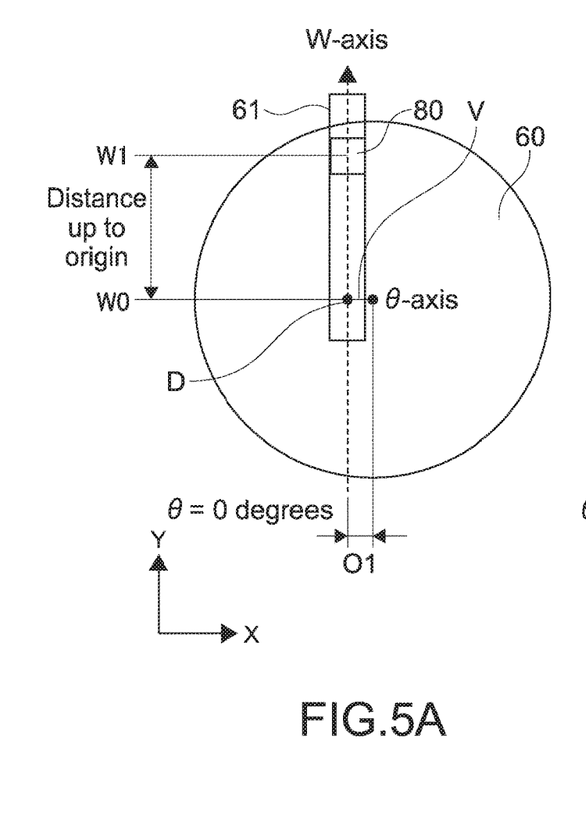
FIGS. 5A, 5B, and 5C are schematic diagrams for describing an exemplary calculation of a first-offset amount.
Figure 5B:
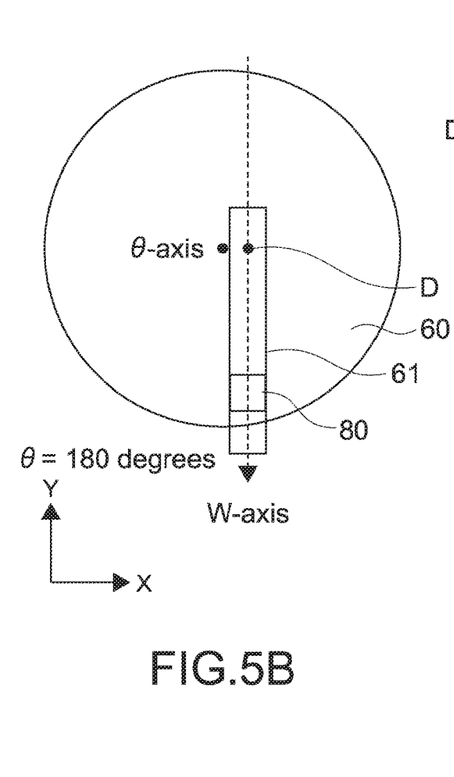
Figure 5C:
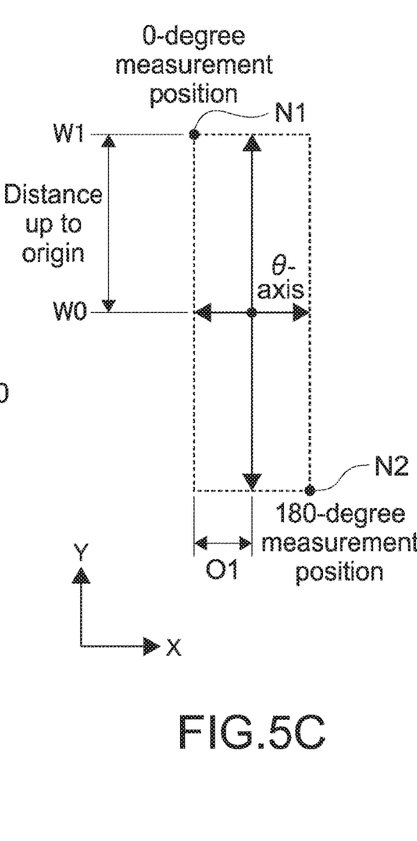
Figure 6:
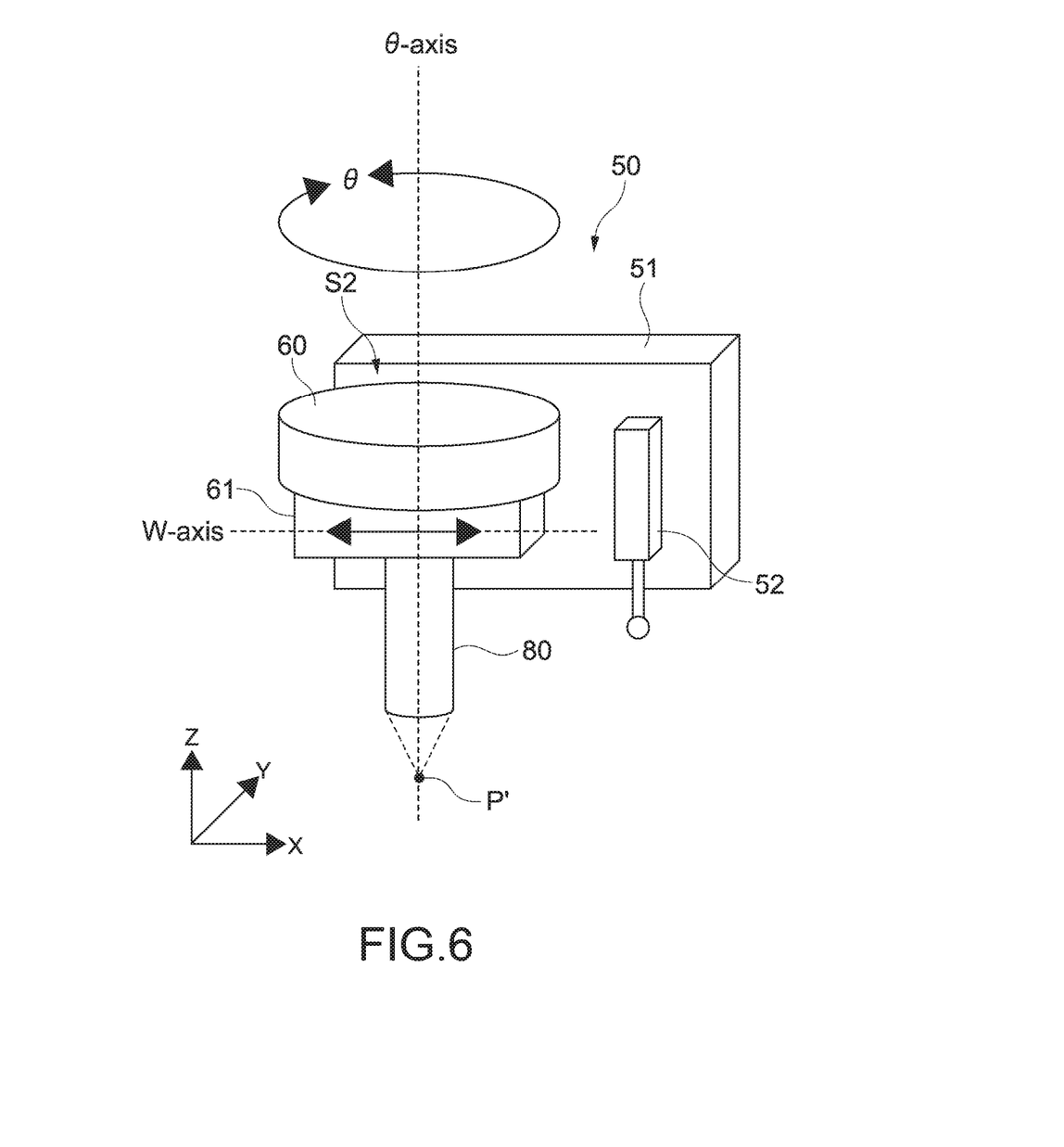
FIG. 6 is a schematic diagram showing an exemplary configuration of an image probe for calibration.

FIGS. 5A to 5C are schematic diagrams for describing an exemplary calculation of a first-offset amount. FIG. 6 is a schematic diagram showing an exemplary configuration of an image probe for calibration 80 attached to the probe head 50 in order to calculate the first offset amount.

As shown in FIG. 5A, a point at which a perpendicular V extending from the $\theta$-axis to the W-axis (in the X-axis direction when the rotational angle is 0 degrees) intersects the W-axis is set to an origin D on the W-axis (W-coordinate is denoted by W0). A distance between the $\theta$-axis and the origin D corresponds to a first offset amount O1.

For calculating the first offset amount O1, the image probe for calibration 80 is, as shown in FIG. 6, attached to the linear drive unit 61 of the probe head 50 instead of the image probe 53. That is, the image probe for calibration 80 is disposed at the second position S2 of the base 51.

The image probe for calibration 80 is configured to be capable of imaging the object to be measured M with the Z-direction being the imaging direction. Thus, a horizontal plane parallel to the XY-plane direction can be measured by the image probe for calibration 80. Note that, as the image probe for calibration 80 is viewed from above along the Z-axis, a focal position P' of the image probe for calibration 80 is the same as the position of the W-coordinate of the image probe for calibration 80 on the W-axis.

For the provision of the image probe for calibration 80, the whole including the image sensor inside the image probe 53 may be replaced by the image probe for calibration 80, for example. Alternatively, only a member that holds the white light interferometric optical system 57 of the image probe 53 may be detachable and replaced by a member that holds an imaging optical system capable of performing imaging in the Z-direction. That is, the image probe for calibration 80 may be disposed at the second position S2 by exchanging only the optical system.

As shown in FIG. 5A, the rotational angle θ is set to 0 degrees and the image probe for calibration 80 is disposed at a position of a W-coordinate W1. A value of the W-coordinate W1 is not limited and a position spaced apart from the origin D by some distance is selected. In this state, a first calibration jig placed on the stage 30 is measured. Note that the position of the probe head 50 in an XYZ-space is appropriately set to a position above the first calibration jig.

For example, a jig having a checker pattern is used as the first calibration jig. The checker pattern is imaged by the image probe for calibration 80 and a position of a predetermined intersection point is measured. As shown in FIG. 5C, the measurement result is stored as a measurement position N1 at 0 degrees.

As shown in FIG. 5B, the rotational drive unit 60 is rotated such that the rotational angle θ becomes 180 degrees while maintaining the position of the probe head 50. The W-coordinate on the W-axis is still the W-coordinate W1. The position of the same intersection point in the same checker pattern is measured under that state. As shown in FIG. 5C, the measurement result is stored as a measurement position N2 at 180 degrees.

As shown in FIG. 5C, a value that is a half of an X-coordinate difference between the measurement position N1 and the measurement position N2 is calculated as the first offset amount O1 between the θ-axis and the origin D. Moreover, a value that is a half of a Y-coordinate difference between the measurement position N1 and the measurement position N2 is calculated as a distance between the origin D and the position of the W-coordinate W1. A W-coordinate W0 of the origin D can be calculated by subtracting the value of that distance from the W-coordinate W1.

On the basis of the first offset amount O1 and the W-coordinate W0 of the origin D, an offset amount between the image probe for calibration 80, which is disposed at a position of an arbitrary W-coordinate at an arbitrary rotational angle θ, and the θ-axis can be calculated. As a matter of course, this offset amount is the same when the image probe 53 is disposed at the second position S2.

Next, a second offset amount between the touch probe 52 and the θ-axis is calculated (Step 102). The second offset amount is a distance between the position of the tip ball 55 and the θ-axis in the XY-plane direction.

Figure 7A:
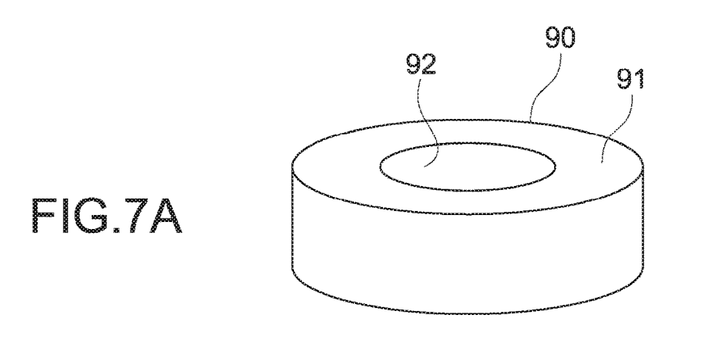
FIGS. 7A, 7B, and 7C are schematic diagrams for describing an exemplary calculation of a second-offset amount.
Figure 7B:
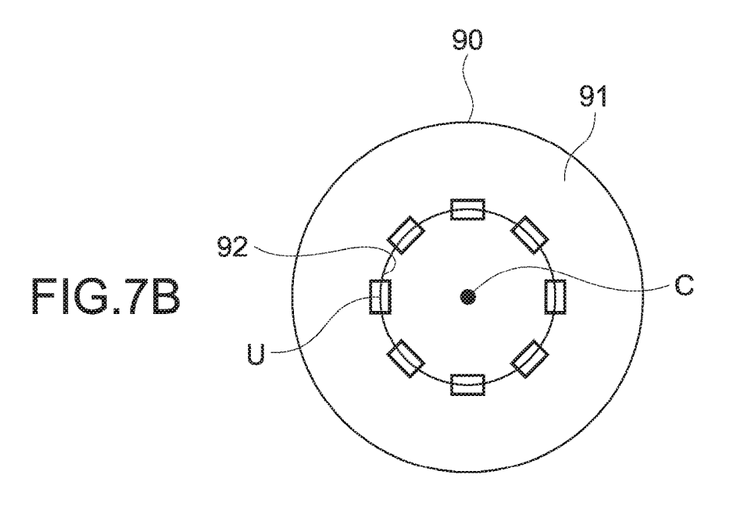
Figure 7C:
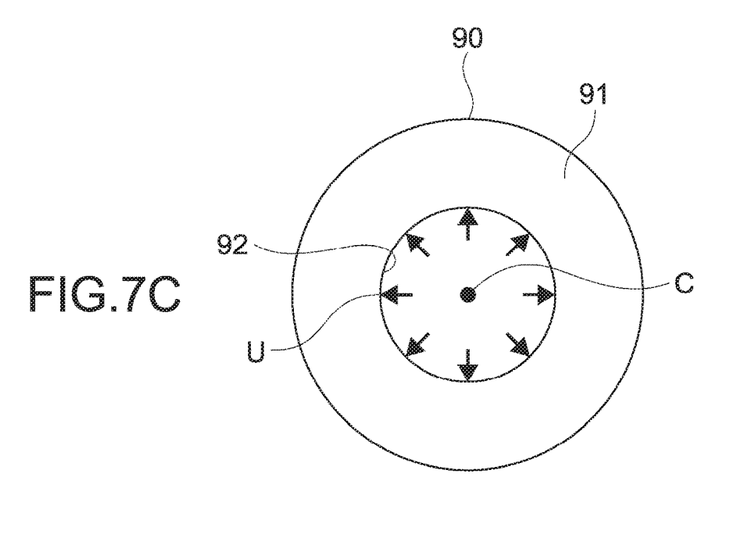

FIGS. 7A to 7C are schematic diagrams for describing an exemplary calculation of a second-offset amount. With the image probe for calibration 80 being attached to the probe head 50, the second calibration jig is measured by each of the touch probe 52 and the image probe for calibration 80.

As shown in FIGS. 7A to 7C, a ring gauge 90 is used as the second calibration jig. Regarding the ring gauge 90, the height of an upper surface 91, the inner diameter of an inner circumferential surface 92, or the like is set to a predetermined calibration value.

First of all, the image probe for calibration 80 is moved to the origin D on the W-axis. Then, focusing on the upper surface 91 of the ring gauge 90 is performed and imaging is performed by the image probe for calibration 80. The inner circumferential surface 92 is, for example, detected by edge detection of a captured image, and X- and Y-coordinates of a center position C are calculated. For example, as shown in FIG. 7B, the entire shape of the inner circumferential surface 92 is calculated on the basis of a plurality of captured images obtained by imaging a plurality of measurement points U set on the inner circumferential surface 92. The X- and Y-coordinates of the center position C are calculated on the basis of the calculation result.

As shown in FIG. 7C, the touch probe 52 scans the ring gauge 90 and positions of the plurality of measurement points U set on the inner circumferential surface 92 are measured. The entire shape of the inner circumferential surface 92 is calculated on the basis of the measurement result, and the X- and Y-coordinates of the center position C are calculated.

A difference (distance) between the X- and Y-coordinates of the center position C as the measurement result obtained by the image probe for calibration 80 and the X- and Y-coordinates of the center position C as the measurement result obtained by the touch probe 52 is calculated. This difference corresponds to an offset amount between the image probe for calibration 80 disposed at the origin D and the tip ball 55 of the touch probe 52.

By adding the first offset amount O1 to this offset amount, the second offset amount between the touch probe 52 and the θ-axis is calculated. In this embodiment, when the image probe for calibration 80 (image probe 53) is disposed at a position of an arbitrary W-coordinate at an arbitrary rotational angle θ, an offset amount between the touch probe 52 and the image probe for calibration 80 (image probe 53) can be calculated on the basis of the first offset amount O1, the W-coordinate W0 of the origin D, and the second offset amount.

A distance up to the focal position P of the image probe 53 shown in FIG. 2 is calculated (Step 103). The calculation for the distance up to the focal position P is performed with the image probe 53 being attached to the probe head 50.

Figure 8A:
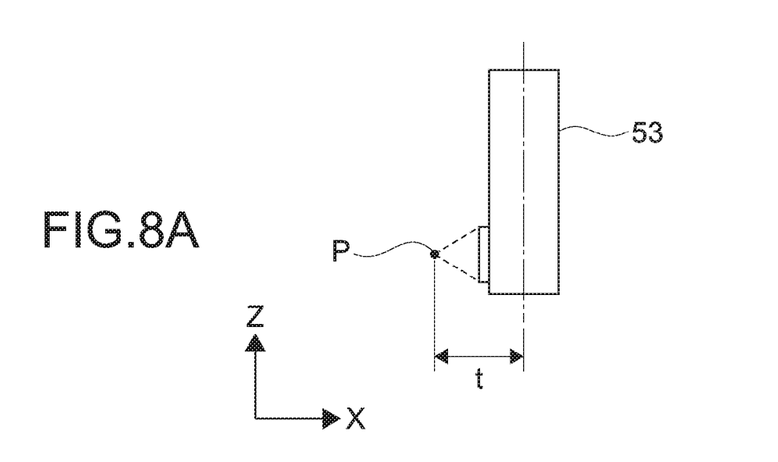
FIGS. 8A and 8B are diagrams for describing an exemplary calculation of a distance up to a focal position of the image probe.
Figure 8B:
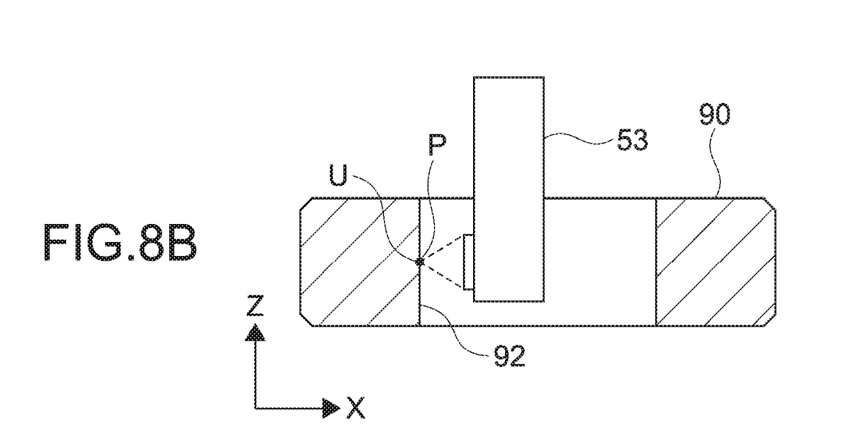

FIGS. 8A and 8B are diagrams for describing an exemplary calculation of the distance up to the focal position P of the image probe 53. The distance up to the focal position P corresponds to a distance t between a W-coordinate of the image probe 53 and a W-coordinate of the focal position P on the W-axis. As shown in FIG. 8A, when the W-coordinate is defined at a center of the image probe 53, it becomes the distance t between the center and the focal position P.

When the image probe 53 is disposed at the origin D, the distance t up to the focal position P on the W-axis corresponds to the offset amount between the θ-axis and the focal position P in the axis direction of the W-axis. Hereinafter, the distance t up to the focal position P of the image probe 53 will be sometimes referred to as a focal distance t of the image probe 53, using the same symbol.

The touch probe 52 scans the ring gauge 90 shown in FIG. 8B and X- and Y-coordinates of the center position are calculated. The ring gauge 90 corresponds to a fourth calibration jig. That is, in this embodiment, the same ring gauge 90 is used as the second calibration jig and the fourth calibration jig. As a matter of course, different calibration jigs may be used.

As described above, an offset amount between the touch probe 52 and the image probe 53 can be calculated on the basis of the first offset amount O1, the W-coordinate W0 of the origin D, and the second offset amount. The image probe 53 is moved to the center position of the ring gauge 90 on the basis of that offset amount. At this time, the image probe 53 is typically disposed at the origin D.

The rotational angle θ is set such that the W-axis extends toward a predetermined measurement point U set on the inner circumferential surface 92. Then, coordinates (θ, W) at which the measurement point U is measured are calculated by causing the image probe 53 to perform scanning in the W-axis direction. Although the image probe 53 is measured in the X-direction in FIG. 7C, the direction of the W-axis is appropriately selected in a manner that depends on the position of the measurement point U.

For example, a plurality of measurement points U as shown in FIG. 7C are measured, and the inner diameter of the inner circumferential surface 92 is calculated on the basis of coordinates (θ, W) of each point U. The focal distance t of the image probe 53 is calculated by comparing the calculated inner diameter with a calibration value for the inner diameter that is set in the ring gauge 90. With this, an offset amount between the position of the tip ball 55 of the touch probe 52 and the focal position P of the image probe 53 in the XY-plane direction can be calculated.

An offset amount between the touch probe 52 and the focal position P in the Z-direction is calculated (Step 104). Such offset-amount calculation is performed with the image probe 53 being attached to the probe head 50.

Figure 9A:
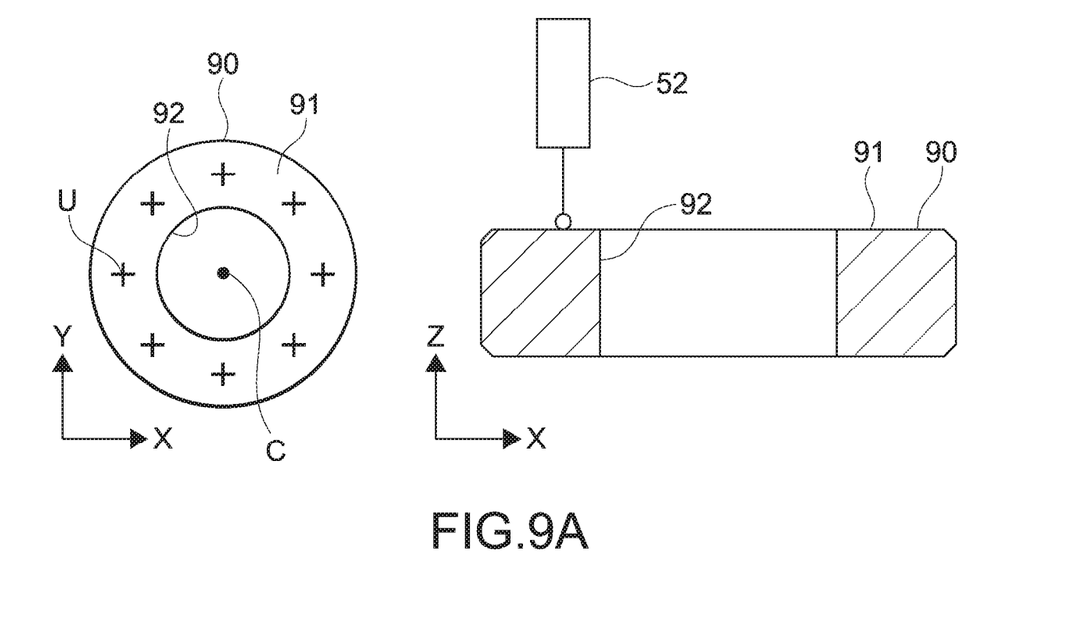
FIGS. 9A and 9B are diagrams for describing an exemplary calculation of an offset amount between the touch probe and the focal position in the Z-direction.

FIGS. 9A and 9B are diagrams for describing an exemplary calculation of the offset amount between the touch probe 52 and the focal position P in the Z-direction. As shown in FIG. 9A, the touch probe 52 scans the ring gauge 90, and X- and Y-coordinates of a center position C and a Z-coordinate of the upper surface 91 are calculated. For example, a Z-coordinate of each of a plurality of measurement points U set on the upper surface 91 is calculated, and a mean value thereof is calculated.

The image probe 53 is disposed at the center position C of the ring gauge 90. Then, a plurality of measurement points U set on an end portion of the inner circumferential surface 92, which is on a side of the upper surface 91, are imaged by the image probe 53. The Z-coordinate of the base 51 at this time is set on the basis of a calibration value for the height of the ring gauge 90, for example.

Figure 9B:
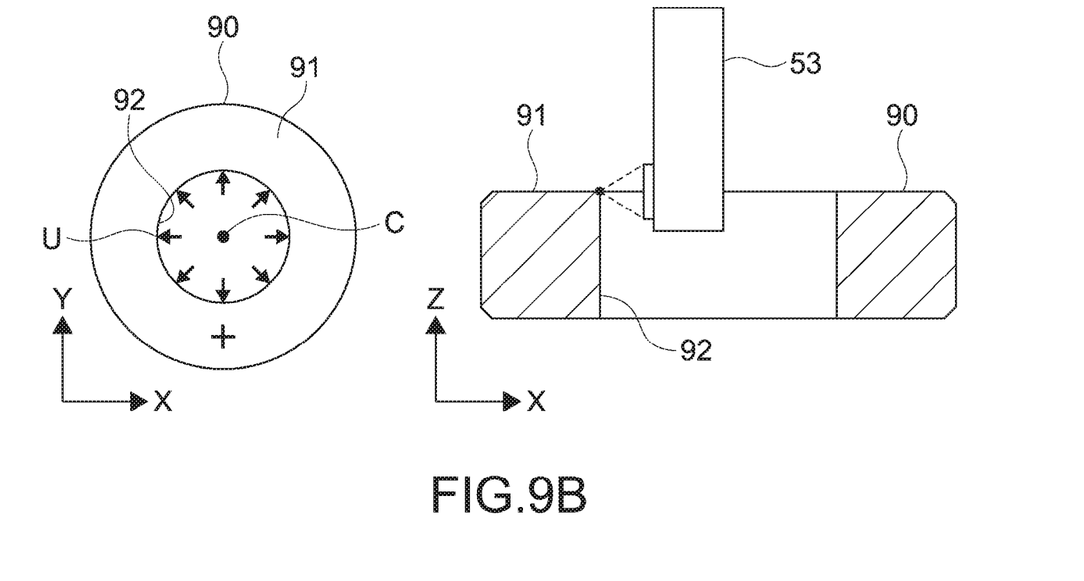

By performing edge detection or the like on an image of the measurement point U captured by the image probe 53, the position of the upper surface 91 (boundary between inner circumferential surface 92 and upper space) is detected. The Z-coordinate of the upper surface 91 is calculated on the basis of the detected position of the boundary. For example, as shown in FIG. 9B, a mean value of Z-coordinates calculated with respect to the plurality of measurement points U is calculated.

A difference (distance) between the Z-coordinate of the upper surface 91 as the measurement result of the touch probe 52 and the Z-coordinate of the upper surface 91 as the measurement result of the image probe 53 is calculated as the offset amount between the touch probe 52 and the focal position P in the Z-direction. With this, an offset amount between the position of the tip ball 55 of the touch probe 52 and the focal position P can be calculated in each of the three axis directions of XYZ.

Note that the ring gauge 90 corresponds to a third calibration jig. Thus, in this embodiment, the same ring gauge 90 is used as the second calibration jig, the third calibration jig, and the fourth calibration jig. As a matter of course, different calibration jigs may be used.

[Inner-Wall Measurement]

Figure 10:
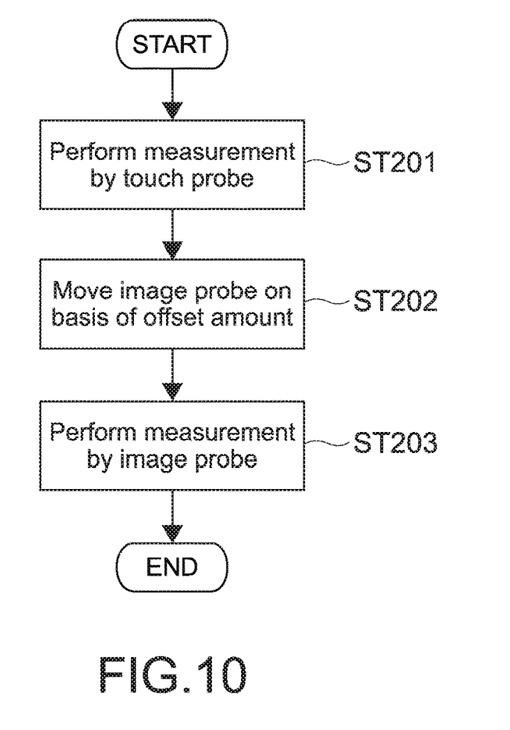
FIG. 10 is a flowchart showing an exemplary inner-wall measurement performed by the inner-wall measuring instrument.
Figure 11A:
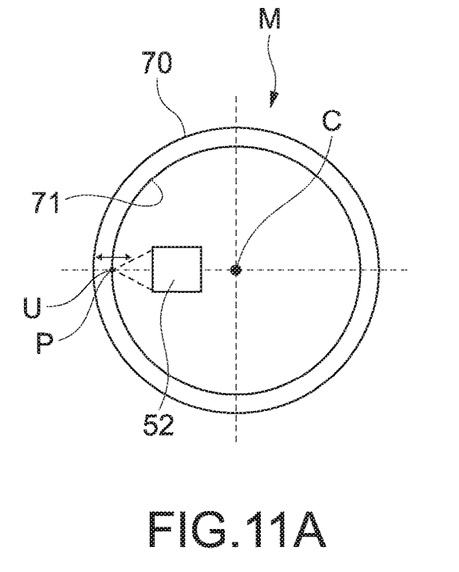
FIGS. 11A and 11B are schematic diagrams for describing steps shown in FIG. 10.
Figure 11B:
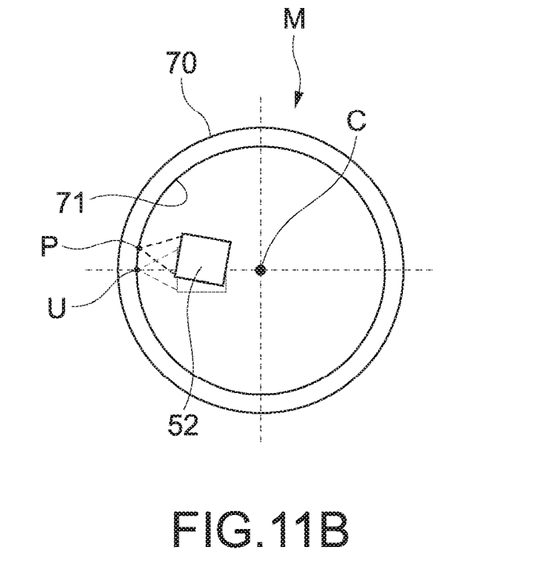

FIG. 10 is a flowchart showing an exemplary inner-wall measurement performed by the inner-wall measuring instrument 500. FIGS. 11A and 11B are schematic diagrams for describing the steps shown in FIG. 10. Hereinafter, the object to be measured M will be referred to as a cylinder block W.

The cylinder block W is measured by the touch probe 52 (Step 101). With this, the height of the upper surface of the cylinder block W, the center position and diameter of each cylinder 70, and the like are measured.

As shown in FIG. 11A, on the basis of the offset amount between the position of the tip ball 55 of the touch probe 52 and the focal position P, the image probe 53 is moved such that the focal position P is at a predetermined measurement point U on an inner wall 71 (Step 202). That is, X-, Y-, and Z-coordinates, a rotational angle θ, and a W-coordinate of the image probe 53 are set on the basis of X-, Y-, and Z-coordinates of the measurement point U and the offset amount.

A specific method of moving the image probe 53 is not limited. For example, the image probe 53 is disposed at the center position C of the cylinder 70, and the rotational angle θ is set such that the W-axis extends toward the measurement point U. Then, the image probe 53 is moved to a predetermined position of the W-coordinate on the W-axis for focusing on the measurement point U.

Note that the focal distance t of the image probe 53 is known, and hence the following processing is also possible. Specifically, a value that is a half (radius) of the inner diameter of the cylinder 70 is displayed as the value of the W-coordinate when the focal position P is set to the measurement point U. This processing makes it easy to know a currently measured position, and hence accurate measurement becomes possible.

The inner wall 71 of the cylinder 70 is measured by the image probe 53 (Step 103). As shown in FIG. 11A, the image probe 53 performs scanning along the W-axis. Moreover, as shown in FIG. 11B, the image probe 53 also performs scanning at the rotational angle θ in a rotation direction of the image probe 53. With this, a surface profile or the like of a region of the inner wall 71, which has the measurement point U as a center, can be highly accurately measured.

As described above, in the inner-wall measuring instrument 500 according to this embodiment, the touch probe 52 and the image probe 53 capable of performing imaging in the XY-plane direction are disposed on the base 51. The image probe 53 is rotated by the rotational drive unit 60 around an axis extending in the Z-direction. Moreover, the image probe 53 is moved by the linear drive unit 61 in the imaging direction. With this, the inner wall 71 of the cylinder 70 or the like can be highly accurately imaged in different imaging directions in the XY-plane direction.

Moreover, in this inner-wall measuring instrument 500, the offset amount between the touch probe 52 and the image probe 53 is calculated by the offset-amount calculator 203. For example, when a plurality of cylinder blocks W are sequentially placed on the placement surface 31, the positions of the cylinder blocks W are often deviated in each placement step, and hence the positions of the cylinders 70 that are measurement targets are often changed.

In this inner-wall measuring instrument 500, first of all, the center position C or the like of each cylinder 70 can be highly accurately calculated by the touch probe 52. Then, on the basis of the offset amount between the both probes, the image probe 53 can be highly accurately moved to a predetermined measurement position. Thus, the inner wall can be measured by the image probe 53 with very high accuracy. Moreover, steps, special configurations, and the like for selecting the both probes become unnecessary, and hence it is also possible to achieve simplification of the measurement steps, reduction in measurement time, a reduction in size of the instrument, and the like.

Moreover, in the offset-amount calculation method according to this embodiment, the image probe for calibration 80 is disposed at the second position S2 at which the image probe 53 is disposed. The use of the image probe for calibration 80 enables the first offset amount and the second offset amount to be highly accurately measured. Moreover, it becomes possible to simplify the calibration work.

OTHER EMBODIMENTS

The present technology is not limited to the above-mentioned embodiment and various other embodiments can be realized.

The offset amount between the touch probe 52 and the image probe 53 is not limited to the offset amount between the position of the tip ball 55 and the focal position P. For example, an offset amount between the position of the tip ball 55 and the position of the image probe 53 may be calculated as the offset amount between the touch probe 52 and the image probe 53. In this case, on the basis of this offset amount, the image probe 53 can be highly accurately moved to the center position C of the cylinder 70 that is calculated by the touch probe 52. Thereafter, focusing is performed by autofocus, for example, and the inner wall 71 is measured.

Hereinabove, the W-coordinate of the origin D on the W-axis is calculated. A design value stored in advance may be used as the W-coordinate of the origin D. That is, highly accurate inner-wall measurement is possible even when only the first offset amount and the second offset amount are calculated as offset amounts in the XY-plane direction.

Hereinabove, the white light interferometer is used as the image probe 53. With this, the surface profile or the like of the inner wall 71 can be highly accurately measured. Note that the present technology is applicable when an image probe different from the white light interferometer is used as the image probe 53.

The number of touch probes 52 and the number of image probes 53 that are provided in the probe head 50 are not limited. The present technology is applicable also when three or more probes are provided.

When the image probe 53 is used, the touch probe 52 may be retractable from the first position S1 of the base 51. For example, a configuration movable to another position within the head cover 40 is conceivable. Similarly, when the touch probe 52 is used, the image probe 53 may be retractable from the second position S2 of the base.

At least two of the characteristic parts of the above-mentioned embodiments may be combined. Moreover, the above-mentioned various effects are merely examples and not limitative and other effects may be produced.

What is claimed is:

1. An inner-wall measuring instrument, comprising:
    a placement surface on which an object to be measured is placed;
    a base relatively movable with respect to the placement surface in three axis directions orthogonal to one another;
    a touch probe that is disposed at a first position of the base and brought into contact with the object to be measured;
    an image probe that is disposed at a second position of the base and configured to image the object to be measured along an imaging direction, the imaging direction being parallel to the placement surface;
    a rotational drive unit that rotates the image probe around an axis extending in a direction perpendicular to the placement surface;
    a linear drive unit that moves the image probe in the imaging direction; and
    a calculator that calculates an offset amount between the touch probe disposed at the first position and the image probe disposed at the second position.

2. The inner-wall measuring instrument according to claim 1, wherein
    the base is relatively movable with respect to the placement surface in a first direction perpendicular to the placement surface, a second direction orthogonal to the first direction, and a third direction orthogonal to each of the first direction and the second direction, and
    the rotational drive unit rotates the image probe around an axis extending in the first direction.

3. The inner-wall measuring instrument according to claim 1, wherein
    the touch probe includes a tip end portion that is brought into contact with the object to be measured,
    the image probe includes an imaging optical system that images the object to be measured, and
    the calculator calculates an offset amount between a position of the tip end portion of the touch probe and a focal position of the imaging optical system of the image probe.

4. The inner-wall measuring instrument according to claim 3, wherein
    the imaging optical system is a light interferometric optical system.

5. The inner-wall measuring instrument according to claim 1, wherein
    the calculator calculates each of a first offset amount between a rotation axis of the image probe rotated by the rotational drive unit and a movement axis of the image probe moved by the linear drive unit and a second offset amount between the touch probe and the rotation axis, and calculates the offset amount on the basis of the calculated first and second offset amounts, the first offset amount and the second offset amount being in the direction parallel to the placement surface.

6. The inner-wall measuring instrument according to claim 5, wherein
    the calculator calculates the first offset amount on the basis of a result of measurement performed on a first calibration jig by the image probe for calibration in a state in which the image probe for calibration is disposed at the second position, the image probe for calibration being configured to image the object to be measured along the imaging direction, the imaging direction being perpendicular to the placement surface.

7. The inner-wall measuring instrument according to claim 6, wherein
    the calculator calculates the second offset amount on the basis of a result of measurement performed on a second calibration jig by each of the touch probe and the image probe for calibration in a state in which the image probe for calibration is disposed at the second position.

8. The inner-wall measuring instrument according to claim 7, wherein
    the calculator calculates an offset amount between the touch probe and the image probe in the direction perpendicular to the placement surface on the basis of a result of measurement performed on a third calibration jig by each of the touch probe and the image probe in a state in which the image probe is disposed at the second position.

9. The inner-wall measuring instrument according to claim 8, wherein
the calculator calculates a distance up to a focal position of the image probe on the basis of a result of measurement performed on a fourth calibration jig by the image probe in a state in which the image probe is disposed at the second position, and calculates the offset amount on the basis of the calculated distance up to the focal position.

10. The inner-wall measuring instrument according to claim 1, wherein that the touch probe extends in a direction perpendicular to the imaging direction.

11. The inner-wall measuring instrument according to claim 1, wherein the image probe and the touch probe are configured such that the touch probe does not intersect with the imaging direction of the image probe.

12. The inner-wall measuring instrument according to claim 1, wherein only one of the touch probe or the image probe is operated at a time.

13. An offset-amount calculation method for calculating an offset amount between a touch probe disposed at a first position of a base, which is relatively movable in three axis directions orthogonal to one another with respect to a placement surface on which an object to be measured is placed, and an image probe disposed at a second position of the base, the method comprising:
    calculating a first offset amount in a direction parallel to the placement surface between a rotation axis and a movement axis of the image probe,
    the image probe configured to
        image the object along an imaging direction, the imaging direction being parallel to the placement surface,
        be rotated by a rotational drive unit around the rotation axis extending in a direction perpendicular to the placement surface, and
        be moved by a linear drive unit along the movement axis extending in the imaging direction;
    calculating a second offset amount in the direction parallel to the placement surface between the touch probe and the rotation axis; and
    calculating an offset amount between the touch probe and the image probe on the basis of the calculated first and second offset amounts.

14. The offset-amount calculation method according to claim 13, wherein
the calculating of the first offset amount includes
    disposing the image probe for calibration at the second position, the image probe for calibration being configured to image the object to be measured along the imagining direction, the imaging direction being perpendicular to the placement surface, and
    causing the image probe for calibration to measure a first calibration jig in a state in which the image probe for calibration is disposed at the second position and calculating the first offset amount on the basis of the measurement result of the first calibration jig.

15. The offset-amount calculation method according to claim 14, wherein
the calculating of the second offset amount includes
    causing each of the touch probe and the image probe for calibration to measure a second calibration jig in a state in which the image probe for calibration is disposed at the second position and calculating the second offset amount on the basis of the measurement result of the second calibration jig.

16. The offset-amount calculation method according to claim 15, further comprising
calculating an offset amount between the touch probe and the image probe in the direction perpendicular to the placement surface.

17. The offset-amount calculation method according to claim 16, wherein
the calculating of the offset amount in the direction perpendicular to the placement surface includes
    disposing the image probe at the second position, and causing each of the touch probe and the image probe to measure a third calibration jig in a state in which the image probe is disposed at the second position and calculating the offset amount in the direction perpendicular to the placement surface on the basis of the measurement result of the third calibration jig.

18. The offset-amount calculation method according to claim 17, further comprising
calculating a distance up to a focal position of the image probe on the basis of a result of measurement performed on a fourth calibration jig by the image probe in a state in which the image probe is disposed at the second position.

* * * * *